United States Patent
Zheng et al.

(10) Patent No.: US 8,323,465 B2
(45) Date of Patent: Dec. 4, 2012

(54) THREE-DIMENSIONALLY ORDERED MACROPOROUS SENSOR APPARATUS AND METHOD

(75) Inventors: Zhi Zheng, Shanghai (CN); Linan Zhao, Shanghai (CN); Marilyn Wang, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 320 days.

(21) Appl. No.: 12/570,211

(22) Filed: Sep. 30, 2009

(65) Prior Publication Data
US 2011/0073473 A1   Mar. 31, 2011

(51) Int. Cl.
G01N 27/30  (2006.01)
(52) U.S. Cl. .................. 204/400; 204/403.01; 204/431; 204/424
(58) Field of Classification Search ............. 204/403.01–403.15, 400, 424–428, 204/431; 205/777.5, 778, 792; 73/31.06
See application file for complete search history.

(56) References Cited

U.S. PATENT DOCUMENTS

| | | | |
|---|---|---|---|
| 6,214,205 B1 * | 4/2001 | Willner et al. | 205/777.5 |
| 6,680,013 B1 | 1/2004 | Stein et al. | |
| 6,991,941 B1 * | 1/2006 | Seul | 436/534 |
| 7,232,511 B1 | 6/2007 | Venkatasetty | |
| 7,279,081 B2 | 10/2007 | Maeno et al. | |
| 2004/0067163 A1 | 4/2004 | Prasad et al. | |
| 2004/0241531 A1 | 12/2004 | Biegert et al. | |
| 2008/0011050 A1 | 1/2008 | Ku et al. | |
| 2008/0149499 A1 | 6/2008 | Ding et al. | |
| 2009/0176079 A1 | 7/2009 | Cabrera-Perez et al. | |

FOREIGN PATENT DOCUMENTS

EP   1 217 360 A2   6/2002

OTHER PUBLICATIONS

Hawley's Condensed Chemical Dictionary entry for "complexing agent", 14th Ed., John Wiley and Sons, 2002.*
Bai et al. "Enzyme-free glucose sensor based on a three-dimensional gold film electrode," Sensors and Actuators B, 134 (2008) 471-476 ("Bai"). "Available online May 28, 2008."*
Acciarri et al. "Ruthenium(Platinum)—Doped Tin Dioxide Inverted Opals for Gas Sensors: Synthesis, Elecron Paramagnetic Resonance, Mössbauer, and Electrical Investigation," Chem. Mater. 2005, 17, 6167-6171.*

(Continued)

Primary Examiner — Alex Noguerola
(74) Attorney, Agent, or Firm — Kermit D. Lopez; Luis M. Ortiz; Ortiz & Lopez, PLLC

(57) ABSTRACT

A three-dimensionally ordered macroporous sensor apparatus and method of forming the same. A direct opal film associated with a number of pores can be formed by vertical deposition of one or more nanospheres on a glass substrate. The thickness of the direct opal film can be controlled by concentration of the nanospheres. A mixture of a precursor/monomer of a sensing material and a complexing agent can be filled into the pores associated with the direct opal film, such that the mixture permeates the interstitial spaces between the pores. The nanospheres may then be removed in order to form a three dimensionally-ordered macroporous electrode with an inverse opal structure. Optionally, the sensing material can be coated on an inverse opal backbone structure formed from an external inactive material and utilizing a coating operation.

17 Claims, 3 Drawing Sheets

OTHER PUBLICATIONS

Honda "Confined Stimuli-Responsive Polymer Gel in Inverse Opal Polymer Membrane for Colorimetric Glucose Sensor," Langmuir 2009, 25(14), 8349-8356 published on Web Jun. 15, 2009.*
Yang et al. "Inverse Opal of Polyaniline for Biosensors Prepared by Electrochemical and Self-Assembly Techniques," Journal of the Electrochemical Society, 155 (1) J23-J25 (2008) pp. 994-1001.*
Ma, X. et al., "Rapid response behavior, at room temperature, of a nanofiber-structured $TiO_2$ sensor to selected simulant chemical-warfare agents," *Anal. Bioanal. Chem.* (2008) 390:1133-1137.
Stein, A., "Sphere templating methods for periodic porous solids," *Microporous and Mesoporous Materials* (2001) 44-45:227-239.
Yamada, H. et al., "Interconnected macroporous $TiO_2$ (anatase) as a lithium insertion electrode material," *Solid State Ionics* (2004) 175:195-198.
Zhu, Y. et al., "Immobilization of horseradish peroxidase in three-dimensional macroporous $TiO_2$ matrices for biosensor applications," *Electrochimica Acta* (2009) 54:2823-2827.
EP Search Report for EP Application No. 10176086 dated Dec. 29, 2010.
U.S. Appl. No. 12/468,769, filed May 19, 2009, Zheng et al.
Lee, S.-K. et al., "Pixellated Photonic Crystal Films by Selective Photopolymerization," *Adv. Mater.* (2006) 18:2111-2116.
Tonti, D. et al., "Ordered macroporous lithium manganese oxide spinels as cathodes for lithium batteries," The Electrical Chemical Society meetings http://ecsmeet6.peerx-press.org/ms_files/ecsmeet6/2009/04/24/00004408/00/4408_0_art_0_knmwtv_cnvpdf.pdf.
Blanco, A. et al., "Stacking patterns in thin self-assembled opal films," Instituto de Ciencia de Materiales de Madrid, Madrid, Spain.
Woo, S.-W. et al., "Ni—Sn Alloy with 3 Dimensionally Ordered Macroporous Cylinder Structure as an Anode for Lithium Batteries," Dept. of Applied Chemistry, Tokyo Metropolitan University, Tokyo, Japan.
Kim, S. et al., "Reflection Band Control of Inverse Opal Film with Photoresponse Properties of Push-Pull Type Azobenzene LC Polymers," *Research Letters in Materials Science* (2008) Article ID 962160.
"Polymer opal films shed new kind of light on nature," PHYSorg.com Jul. 23, 2007, www.physorg.com/news104427587.html.
Sorensen, E. M. et al., "Three-Dimensionally Ordered Macroporous $Li_4Ti_5O_{12}$: Effect of Wall Structure on Electrochemical Properties," *Chem. Mater.* (2006) 18:482-489.
Lytle, J. C. et al., "Fabrication of Three-Dimensionally Ordered Macroporous (3DOM) Electrode Materials," Department of Chemistry, University of Minnesota.
Tonti, D. et al., "Ordered macroporous lithium manganese oxide spinels as cathodes for lithium batteries," 59th Annual Meeting of the International Society of Electrochemistry Sep. 7-12, 2008, Seville, Spain (Abstract) http://event08.ise-online.org/site/files/ise081996.pdf.

* cited by examiner

THREE-DIMENSIONALLY ORDERED MACROPOROUS SENSOR APPARATUS AND METHOD

TECHNICAL FIELD

Embodiments are generally related to sensing technologies. Embodiments are also related to macroporous sensing materials. Embodiments are additionally related to macroporous sensors.

BACKGROUND OF THE INVENTION

Chemical sensors, particularly biosensors operating with bioactive components, are based on microporous (e.g., pore diameter <20 Å) and mesoporous (e.g., pore diameter 20 Å to 500 Å) materials such as, for example, $SnO_2$ or $WO_3$ films. The chemical structure of such materials permits guest molecules to access large internal void surfaces and cavities, and thereby enhance the catalytic activity and adsorptive capacity of these materials. Examples of microporous materials are aluminosilicate molecular sieves, also known as "zeolites". In zeolites, the micropores form regular arrays of uniformly-sized channels and can function as a host to ionic and neutral molecular guest species. The utility of sensors and devices fabricated from zeolites and other microporous materials, however, is generally limited to those applications where the guest or analyte molecules have sufficiently small kinetic diameters to pass through the narrow microporous void openings.

Mesoporous materials offer the advantage of larger pore sizes, making them compatible with applications such as those involving the separation or sensing of relatively large organic molecules. Mesoporous materials are amorphous or polycrystalline solids such as pillared clays and silicates. Unfortunately, the pores in such materials are often irregularly spaced and broadly distributed in size, making them ill-suited for chemical separations, sensing, and other device-oriented applications. Such microporous and mesoporous materials have very high specific areas. Because the pores are irregular and usually less than 50 nm (or even less than 20 nm), however, the fluent resistance of the sensing material is high and some internal surface is not applicable. Also, such materials are relatively difficult to clean after each usage and the residue of a previous sample can affect new measurements, which are depicted graphically as a floating of the baseline of the sensor.

Based on the foregoing, it is believed that a need exists for an improved three-dimensionally ordered macroporous (3DOM) sensor apparatus. A need also exists for an improved method for fabricating such a 3DOM sensor apparatus, as described in greater detail herein.

BRIEF SUMMARY

The following summary is provided to facilitate an understanding of some of the innovative features unique to the present invention and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved three-dimensionally ordered macroporous (3DOM) sensor apparatus that is capable of providing a high sensitivity and a fast response.

It is another aspect of the disclosed embodiments to provide for an improved method for fabricating a 3DOM sensor apparatus.

The aforementioned aspects and other objectives and advantages can now be achieved as described herein. A three-dimensionally ordered macroporous sensor apparatus and method of forming the same are disclosed. A direct opal film associated with a number of pores can be formed by vertical deposition of one or more nanospheres on a glass substrate. The thickness of the direct opal film is generally controlled by the concentration of the nanospheres. A mixture of a precursor of a sensing material (e.g., $TiO_2$, $SnO_2$, $WO_3$, polyaniline, polypyrrole, polypropylene, metal particles, etc) and a complexing agent can be filled into the pores associated with the direct opal film such that the mixture permeates the interstitial spaces between the pores. The nanospheres may then be removed by a solvent etching process and/or a sintering approach based on the sensing material, in order to form a three dimensionally-ordered macroporous electrode with an inverse opal structure. Optionally, the sensing material can be coated on an inverse opal backbone structure formed by an external inactive material utilizing a coating method (e.g., spin coating, chemical bath deposition, chemical vapor deposition, etc).

The three dimensionally-ordered macroporous electrode can be utilized as a sensing material in association with an electrochemical sensor, a SAW sensor, a QCM sensor, and a F-bar or a piezoelectric sensor. The pores of the macroporous sensor apparatus with inverse opal structure can be closely packed in the context of a face-centered cubic (fcc) structure. The inverse opal backbone structure increases the specific surface area of the sensor apparatus, which in turn greatly enhances its sensitivity and response time. The size of the interconnecting and large pores of the disclosed three dimensionally-ordered macroporous sensor apparatus additionally possesses less resistance to the flow of fluent. Such a fluent may flow fast and freely in the macroporous sensor apparatus and, as a result, the detecting speed is high. The disclosed sensor apparatus may then be readily refreshed by flushing with air/solvent after a detection operation.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

The disclosed embodiments illustrate a method for forming a macroporous structure, preferably a three-dimensional ordered macroporous (3DOM) structure, of many compositions. Significantly, the disclosed approach generally involves the use of a precursor of a sensing material, preferably materials constituting, for example, low viscosity liquids or compounds that are soluble in water, alcohols, or other solvents, which are further compatible with a direct opal film. The disclosed embodiments are based on precipitation within the interstitial spaces of the opal film, subsequent chemical conversion of the precursors if necessary, and removal of the material forming the opal film. The resultant macroporous material generally includes a framework with voids (e.g., pores) and windows in the walls of the framework between the voids, thereby forming open channels between the voids.

Figure 1:
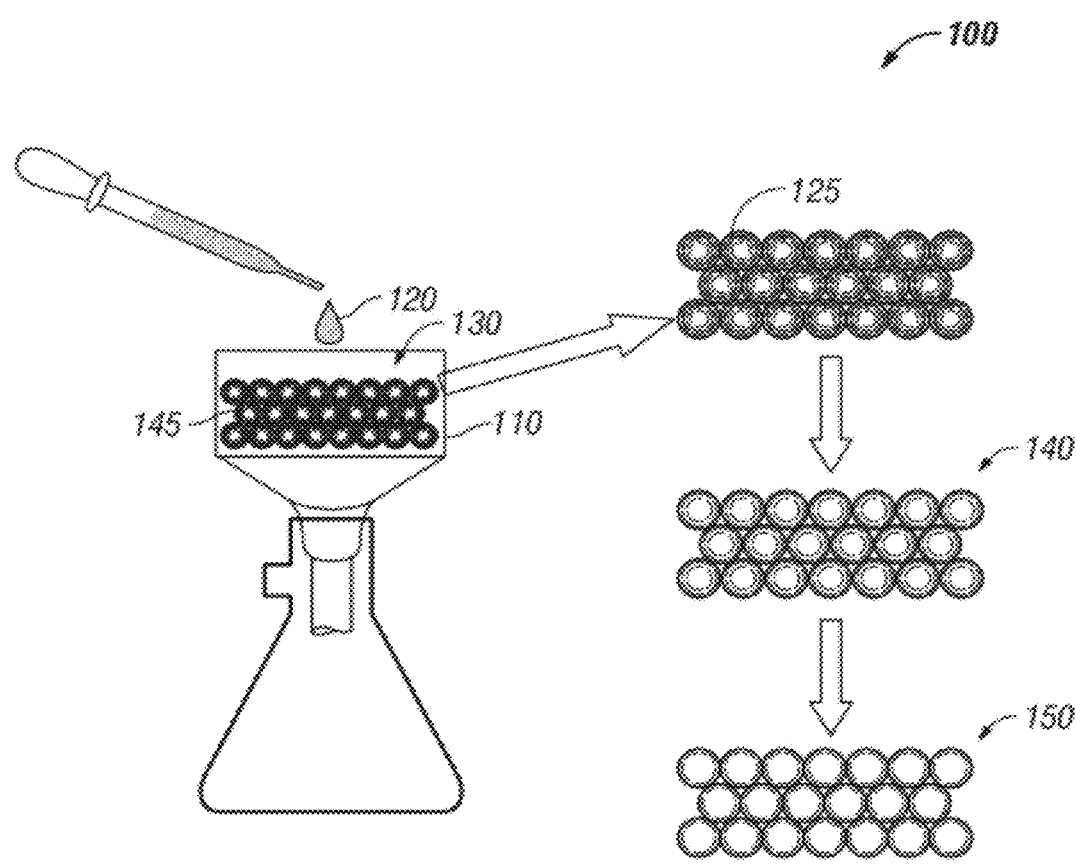
FIG. 1 illustrates a schematic view of the formation of a three-dimensionally ordered macroporous electrode, in accordance with an embodiment.

FIG. 1 illustrates a schematic view of a method 100 of forming a three-dimensionally ordered macroporous (3DOM) electrode 150, in accordance with an embodiment. The 3DOM electrode 150 can be utilized as a sensing material in a wide range of sensing applications including, but not limited to, electrochemical sensors, SAW (Surface Acoustic Wave) sensors, QCM sensors, and F-bar or other types of piezoelectric sensors. The 3DOM electrode 150, when utilized with such sensors, can provide a high sensitivity and a fast response time. As further indicated in FIG. 1, a direct opal film 130 associated with a number of pores 145 can be formed by vertical deposition of one or more nanospheres 125 on a glass substrate 110.

Figure 2:
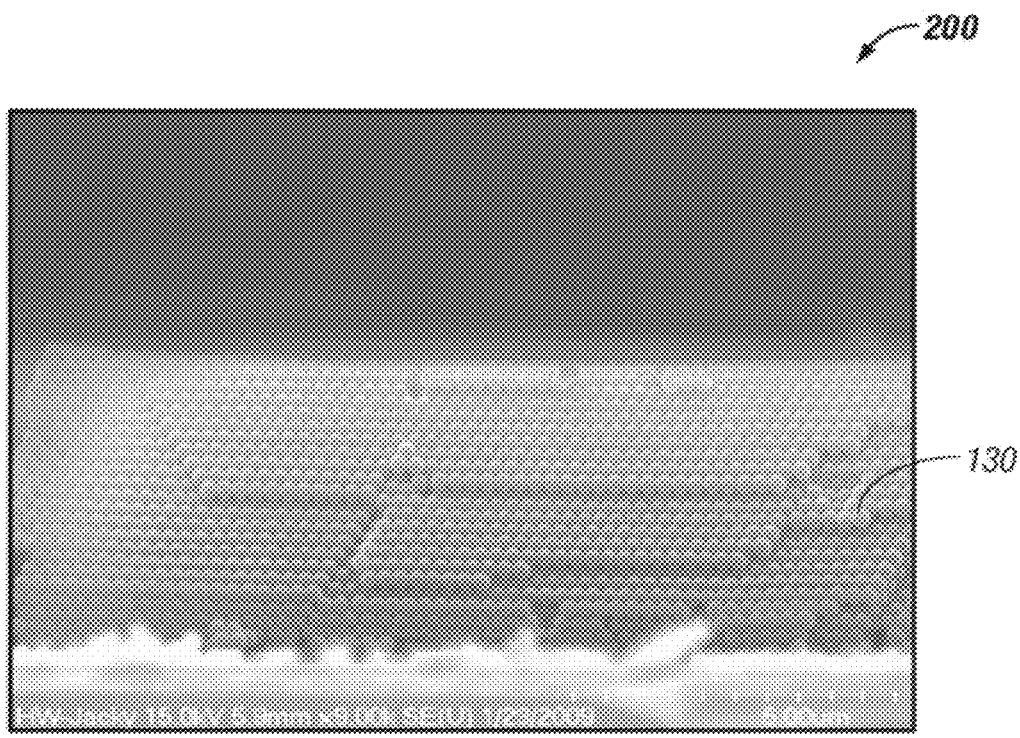
FIG. 2 illustrates a screen shot of a scanning electron micrograph of a film with an opal structure, in accordance with an embodiment.

FIG. 2 illustrates a scanning electron micrograph 200 of the direct opal film 130 with the opal structure of the direct opal film 130 depicted in FIG. 1, in accordance with an embodiment. The thickness of the direct opal film 130 can be controlled by the concentration of the nanospheres 125 illustrated in FIG. 1. The concentration of the nanospheres 125 permits control over the phase and thickness of the walls of the direct opal film 130, as well as interconnectivity between the pores 145 of the 3DOM electrode 150. A mixture 120 comprising a precursor of a sensing material and a complexing agent can be filled into the pores 145 associated with the direct opal film 130. The complexing agent forms a complex compound in association with the sensing material. Note that the sensing material can be configured from $TiO_2$, $SnO_2$, $WO_3$, polyaniline, polypyrrole, polypropylene, and metal particles, etc., depending upon design considerations. It can be appreciated that other type of materials may be utilized in place of such suggested materials.

The precursor and the complexing agent can be added to the direct opal film 130 in a manner that permits the mixture 120 to permeate the interstitial spaces between the particles, preferably, close-packed particles. The precursor can be a liquid, a solid, or a gas. Typically, the precursor is a solid or a liquid dissolved in one or more solvents in which one or more precursors are soluble. An inorganic precursor may be utilized without a solvent if it is a liquid with such a sufficiently low viscosity that it can permeate the interstitial spaces. If necessary for the liquid precursors, a solvent may be utilized to adjust the viscosity and the rate of penetration.

The mixture 120 can be added to the direct opal film 130 by soaking the direct opal film 130 in the composition, and in certain cases filtering the composition through the direct opal film 130, and so forth. The penetration of the interstitial spaces can occur simply by the action of gravity flow, capillary action, or through the use of pressure differentials such as, for example, those associated with vacuum-assisted percolation. Preferably, the solvent and the method of penetration can be selected to permit the mixture 120 to penetrate the direct opal film 130 and substantially eliminate faults in the final structure as a result of non-wetted regions. The mixture 120 impregnated into the direct opal film 130 can then be converted into a hardened framework around the direct opal film 130, thereby forming a composite 3DOM material 140. This can occur through several steps and several mechanistic pathways, depending on the type of precursor.

Thereafter, the nanospheres 125 that form the opal film 130 can be removed by a solvent etching process and/or a sintering approach based on the sensing material mixture 120 in order to form a three dimensionally-ordered macroporous electrode 150 with an inverse opal structure. Optionally, the sensing material mixture 120 may be coated on an inverse opal backbone structure that can be formed by an external inactive material. The inverse opal backbone structure can be formed utilizing different coating methods such as, for example, a spin coating, a chemical bath deposition, and a chemical vapor deposition, etc. The majority of the novel materials produced offer distinct advantages over previously synthesized macroporous structures due to the remarkable three-dimensional periodicity and uniformity of the macropores that are separated by dielectric walls.

Figure 3:
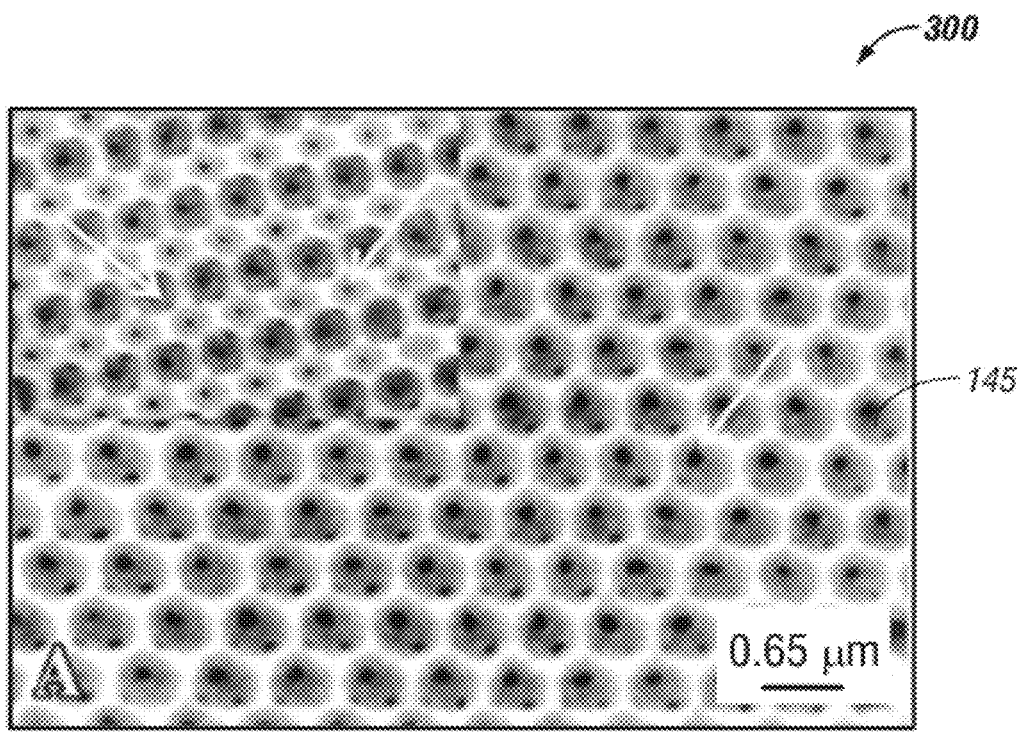
FIG. 3 illustrates a screen shot of a 3DOM $TiO_2$ electrode sample with an inverse opal structure, in accordance with an embodiment.

FIG. 3 illustrates a 3DOM $TiO_2$ electrode sample 300 with inverse opal structure, in accordance with an embodiment. Note that in FIGS. 1-4, identical or similar blocks are generally indicated by identical reference numerals. In the example depicted in FIG. 3, the diameter of the pores 145 of the 3DOM $TiO_2$ electrode sample 300 is 325 nm and the pores 145 are closely packed in a face-centered cubic (fcc) structure. The $TiO_2$ backbone of the 3DOM $TiO_2$ electrode sample 300 is actually an interconnecting network of many 20-30 nm $TiO_2$ granules, which further increases the specific surface area of the 3DOM $TiO_2$ electrode sample 300.

The pores 145 associated with the 3DOM electrode 150 increases the surface area and produce more surface sites, which enhance the sensitivity and response speed greatly of the resulting sensor. The 3DOM electrode 150 can provide for a high performance capability by maintaining high capacities as discharge rates are increased. In addition to material properties of the 3DOM electrode 150, attributes such as particle size and morphology can also be optimized. The inverse opal structure of the 3DOM electrode 150 also minimizes the diffusion pathway lengths and provides improved electrode properties in the sensor applications. Sensor systems that utilize the 3DOM electrode 150 can permit electrodes to sustain improved capacities at high discharge rates and retain high capacities even at extremely high discharge rates.

Figure 4:
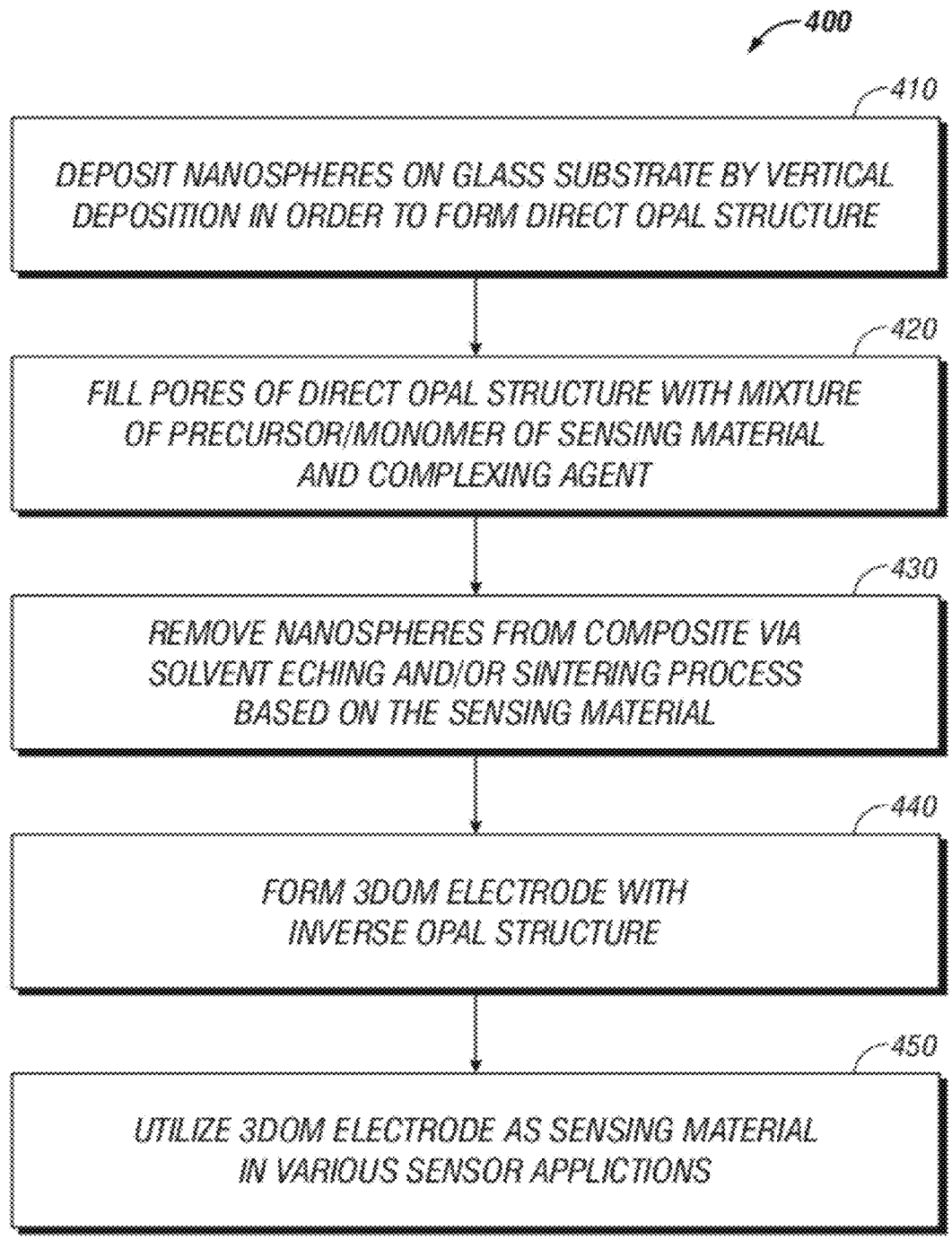
FIG. 4 illustrates a detailed flow chart of operations illustrating logical operational steps of method for forming the disclosed three-dimensionally ordered macroporous sensor apparatus, in accordance with an embodiment.

FIG. 4 illustrates a detailed flow chart of operations illustrating logical operational steps of method 400 for forming a three-dimensionally ordered macroporous sensor apparatus, in accordance with an embodiment. The 3DOM electrode 150 can provide enhanced control of the voltage applied to the sensor and thus improve the selectivity of the sensor utilizing the disclosed 3DOM device. The materials formed by the method 400 possess a macroporous structure. The direct opal film 130 associated with one or more pores 145 can be formed by vertical deposition of the nanospheres 125 on to the glass substrate 110, as illustrated at block 410. Further, the pores 145 of the direct opal film 130 can be filled with the mixture 120 of the precursor/monomer of sensing material and the complexing agent, as depicted at block 420.

The nanospheres 125 can be removed from the composite via solvent etching and/or sintering based on the sensing material, as indicated at block 430. The 3DOM electrode 150 with the inverse opal structure can then be formed, as illustrated at block 440. The 3DOM electrode 150 can be utilized as a sensing material in various sensor applications, as depicted at block 450. The 3DOM electrode 150 described herein can generate a signal utilizing different sensing approaches such as, but not limited to, voltammetry, surface acoustic wave, quartz crystal microbalance, piezoelectric, F-bar, and SERS, etc. The 3DOM electrode 150 possesses pores on the order of approximately 50 nanometers (nm) in size. Significantly, and preferably, the 3DOM electrode 150 formed by the disclosed method 400 is uniform and preferably ordered. Note that as utilized herein, the term "uniform macroporous material" generally refers to materials or structures that possess macro-sized pores that are substantially the same size (e.g., typically, the pore sizes vary by no greater than about 20%). An "ordered" macroporous material possesses at least 10 (and often up to 300 or more) close-packed voids in each of three dimensions.

Certain embodiments of the present invention have uniformly sized macropores, although the order is not as high as for some other materials. Also, significantly, the macroporous structures formed by the disclosed embodiment(s) may be configured in a wide range of sizes. That is, the disclosed technique is suitable for providing film-like articles as well as much thicker articles. The size of the interconnecting and large pores of the 3DOM electrode 150 possesses less resistance to the flow of fluent. The fluent flows fast and freely in the disclosed 3DOM sensor apparatus and as a result, the detection speed is high, and the disclosed sensor apparatus can be easily refreshed by flushing with air/solvent after a detection operation. When implemented, the method 400 can provide for a sensing apparatus that is highly sensitive during sensing operations.

It will be appreciated that variations of the above-disclosed and other features and functions, or alternatives thereof, may be desirably combined into many other different systems or applications. For example, the disclosed three-dimensional ordered macroporous sensing apparatus may be utilized not only for detecting, for example, organophosphate pesticides, but also for detecting other gas/chemicals. Also, it will be appreciated that various presently unforeseen or unanticipated alternatives, modifications, variations or improvements therein may be subsequently made by those skilled in the art which are also intended to be encompassed by the following claims.

What is claimed is:

1. A three-dimensionally ordered macroporous apparatus, said apparatus comprising:
    a glass substrate;
    an opal film having a plurality of pores with a vertical deposition of a plurality of nanospheres on said glass substrate, wherein a thickness of said opal film is controllable by a concentration of said plurality of nanospheres;
    a mixture of a precursor of a sensing material comprising a polymer and a complexing agent, said plurality of pores filled with said mixture, wherein said mixture permeates interstitial spaces between said plurality of pores; and
    wherein said plurality of nanospheres is removable in order to form a macroporous electrode with a formed inverse opal structure, said macroporous electrode configured for use with a sensor and comprising said glass substrate, said opal film, and said plurality of pores.

2. The apparatus of claim 1 wherein said macroporous electrode comprises an ordered, three-dimensional structure.

3. The apparatus of claim 1 wherein said sensing material comprising a polymer is coated on an inverse opal backbone structure comprising an external inactive material.

4. The apparatus of claim 3 wherein said formed inverse opal backbone structure is configured from a process selected from a group of processes comprising at least one of the following types of processes:
    spin coating;
    chemical bath deposition; and
    chemical vapor deposition.

5. The apparatus of claim 1 wherein said macroporous electrode comprises a three dimensionally-ordered macroporous electrode.

6. The apparatus of claim 1 wherein said precursor of said sensing material comprising a polymer comprises at least one of the following types of polymers:
    polyaniline;
    polypyrrole; and
    polypropylene.

7. The apparatus of claim 1 wherein said plurality of nanospheres is removable via a process selected from a group comprising at least one of the following types of processes:
    solvent etching; and
    sintering.

8. The apparatus of claim 1 wherein:
    said macroporous electrode comprises an ordered, three-dimensional structure; and
    said sensing material comprising a polymer is coated on said formed inverse opal backbone structure comprising an external inactive material.

9. A three-dimensionally ordered macroporous apparatus, said apparatus comprising:
    a glass substrate;
    an opal film having a plurality of pores with a vertical deposition of a plurality of nanospheres on said glass substrate, wherein a thickness of said opal film is controllable by a concentration of said plurality of nanospheres;
    a mixture of a precursor of a sensing material comprising a polymer and a complexing agent, said plurality of pores filled with said mixture, wherein said mixture permeates interstitial spaces between said plurality of pores;
    wherein said plurality of nanospheres is removable in order to form a macroporous electrode with a formed inverse opal structure, said macroporous electrode configured for use with a sensor and comprising said glass substrate, said opal film, and said plurality of pores;
    wherein said macroporous electrode comprises a three dimensionally-ordered macroporous electrode; and
    wherein said sensing material is coated on an inverse opal backbone structure comprising an external inactive material.

10. The apparatus of claim 9 wherein said precursor of said sensing material comprising a polymer comprises at least one of the following types of polymers:
    polyaniline;
    polypyrrole; and
    polypropylene.

11. The apparatus of claim 9 wherein said plurality of nanospheres is removable via a process selected from a group comprising at least one of the following types of processes:
    solvent etching; and
    sintering.

12. A method of configuring a three-dimensionally ordered macroporous apparatus, said method comprising:
    configuring an opal film having a plurality of pores with a vertical deposition of a plurality of nanospheres on a glass substrate;
    controlling a thickness of said opal film by varying a concentration of said plurality of nanospheres;

forming a mixture of a precursor of a sensing material comprising a polymer and a complexing agent, said plurality of pores filled with said mixture, wherein said mixture permeates interstitial spaces between said plurality of pores; and removing said plurality of nanospheres in order to form a macroporous electrode with an inverse opal structure, said macroporous electrode configured for use with a sensor and comprising said glass substrate, said opal film, and said plurality of pores.

13. The method of claim 12 further comprising configuring said macroporous electrode to comprise an ordered, three-dimensional structure.

14. The method of claim 12 further comprising coating said sensing material comprising a polymer on an inverse opal backbone structure comprising an external inactive material.

15. The method of claim 14 wherein said inverse opal backbone structure is configured from a process selected from a group of processes comprising at least one of the following types of processes:

spin coating;
chemical bath deposition; and
chemical vapor deposition.

16. The method of claim 12 further comprising configuring said macroporous electrode as a three dimensionally-ordered macroporous electrode.

17. The method of claim 12 further comprising:

configuring said precursor of said sensing material comprising a polymer comprises at least one of the following types of polymers:
polyaniline;
polypyrrole;
polypropylene;

removing said plurality of nanospheres via a process selected from a group comprising at least one of the following types of processes:
solvent etching; and
sintering.

* * * * *